(12) United States Patent
Czichos et al.

(10) Patent No.: US 6,908,764 B2
(45) Date of Patent: Jun. 21, 2005

(54) RECOMBINANT HUMAN CELL FOR BONE AND CARTILAGE CELL FORMATION

(75) Inventors: Stefan Czichos, Braunschweig (DE); Joerg Lauber, Braunschweig (DE); Hubert Mayer, Braunschweig (DE); Gerhard Gross, Braunschweig (DE)

(73) Assignee: Yissum Research Development Company, Jerusalem (IL)

( * ) Notice: Subject to any disclaimer, the term of this patent is extended or adjusted under 35 U.S.C. 154(b) by 120 days.

(21) Appl. No.: 10/190,963

(22) Filed: Jul. 8, 2002

(65) Prior Publication Data

US 2003/0036523 A1 Feb. 20, 2003

Related U.S. Application Data

(63) Continuation of application No. 09/376,276, filed on Aug. 18, 1999, now abandoned.

(30) Foreign Application Priority Data

Aug. 18, 1998 (DE) .......................................... 198 37 438

(51) Int. Cl.[7] .............................. C12N 5/00; C12N 5/06; C12N 5/08; C12N 15/63
(52) U.S. Cl. ...................... 435/325; 435/352; 435/363; 435/366; 435/372; 435/455
(58) Field of Search ................... 435/325, 352, 435/363, 366, 372, 455, 377, 320.1

(56) References Cited

PUBLICATIONS

Allay, J.A. et al., LacZ and interleukin–3 expression in vivo after retroviral transduction of marrow–derived human osteogenic mesenchymal progenitors. *Human gene thereapy* 8:1417–1427, 1997.
Bulfone et al., T–Brain–1: A Homolog of Brachyury Whose Expression Defines Molecularly Distinct Domains Within the Cerebral Cortex, *Neuron*, 15:63–78, Jul. 1995.
Chapman et al., Expression of the T–Box Family Genes, Tbx1–Tbx5, During Early Mouse Development, *Developmental Dynamics*, pp. 379–390, Feb. 7, 1996.
Chapman et al., Three Neural Tubes in Mouse Embryos with Mutations in the T–Box gene Tbx6, *Nature* 391:695–697, Feb. 12, 1998.

de Angelis et al., Promotion of Gastrulation by Maternal Growth Factor in Cultured Rabbit Blastocysts, *Cell & Tissue Research*, pp. 147–154, May 17, 1995.
Deonarain; Ligand–targeted receptor–mediated vectors for gene delivery, *Exp. Opin. Ther. Patenrts* 8(1):53–69, 1998.
Herrmann et al., Cloning of the T Gene Required in Mesoderm Formation in the Mouse, *Nature* 343:617–622, Feb. 15, 1990.
Jim Smith, Brachyury and the T–Box Genes, *Current Opinion in Genetics and Development*, pp. 474–480, 1997.
Kispert et al., Homologs of the Mouse Brachyury Gene are Involved in the Specification of Posterior Terminal Structures in Drosophila, Tribolium, and Locusta, *Genes & Development*, pp. 2137–2150, Jul. 25, 1994.
Kispert et al., The T Protein Encoced by Brachyury is a Tissue–Specific Transcription Factor, *The EMBO Journal* 14:4763–4772, Nov. 19, 1995.
Li et al., Holt–Oram Syndrome is Caused by Mutations in TBX5, a Member of the Brachyury (T) Gene Family, *Nature Genetics* 15:21–29, Jan. 1997.
Li, K.J. et al., Retroviral–mediated gene transfer into human bone marrow stromal cells: Studies of efficiency and in vivo survival in SCID mice. *Eur. J. Haematol.* 55:302–306, 1995.
Miller et al., Targeted vectors for gene therapy, *FASEB J.* 9:190–199, 1995.
Müller et al., Crystallographic Sttructure of the T Domain–DNA Complex of the Brachyury Transcription Factor, *Nature* 389:884–888, Oct. 23, 1997.
Papaioannou et al., The T–Box Gene Family, *BioEssays* 20:9–19, 1998.
Simon et al., A Novel Family of T–Box Genes in Urodele Amphibian Limb Development and Regeneration: Candidate Genes Involved in Vertebrate Forelimb/Hindlimb Patterning, *Development* 124:1355–1366, 1997.
Spranger et al., Muscular Involvement in the Holt–Oram Syndrome, *Med Genet*, pp. 978–981, 1997.
Verma; Gene therapy–promises, problems and prospects; *Nature vol.* 389:239–242, 1997.

*Primary Examiner*—David Guzo
*Assistant Examiner*—Quang Nguyen
(74) *Attorney, Agent, or Firm*—Marshall, Gerstein & Borun LLP

(57) ABSTRACT

The invention relates to a recombinant human cell of undifferentiated mesenchyma for bone and cartilage cell formation, the human cell having the ability to express Tbr-1, Brachyury or another member of the T-box family.

2 Claims, 2 Drawing Sheets

Figure 1:
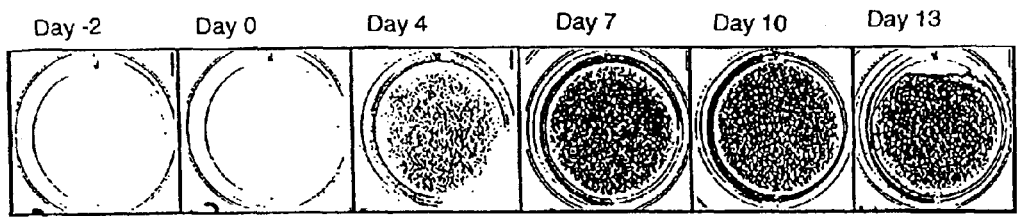
Figure 1:
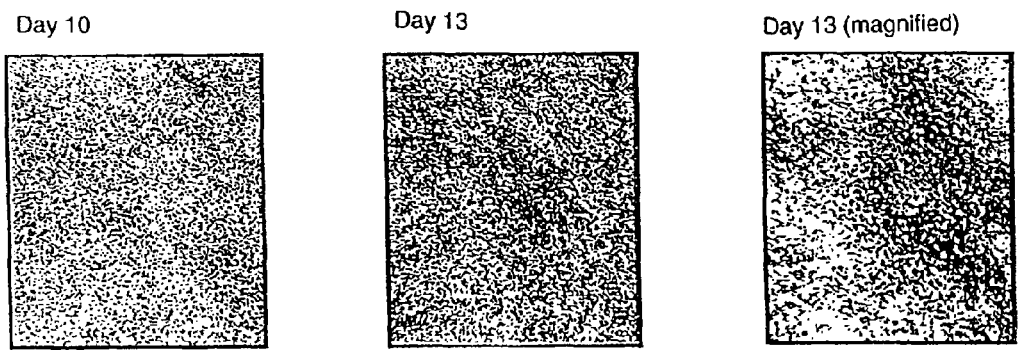

*Brachyury*-induced bone-forming osteoblasts in mesenchymal precursor cells C3H10T½ (alkaline phosphatase histology)

(reaching of confluence: day 0)

*Brachyury*-induced cartilage-forming chondrocytes in mesenchymal precursor cells C3H10T½ (Alcian Blue histology)

(reaching of confluence: day 0)

RECOMBINANT HUMAN CELL FOR BONE AND CARTILAGE CELL FORMATION

This is a continuation of U.S. application Ser. No. 09/376,276, filed Aug. 18, 1999 now abandoned, which in turn claims priority on German Patent No. 198 37 438.0 filed Aug. 18, 1998.

Despite intensive research internationally there is only one transcription factor that is able to trigger the formation of bone-forming osteoblasts at the genetic level. The properties of that factor have been described recently under a number of names: Osf2, Aml3 or Cbfa1, it being the same factor in all cases. A transcription factor for cartilage-forming chondrocytes does not currently exist.

Brachyury (T) is a transcription factor belonging to the so-called T-box family. Its properties and those of the T-box family have recently been described in a number of review articles (Papaioannou & Silver, 1998; Smith, 1997). Brachyury and other members of that family (Tbx1 to Tbx6) are active in early embryonic development (Herrmann et al., 1990; Kispert et al., 1994; De Angelis et al., 1995; Chapman et al., 1996).

Brachyury has been characterised further as a transcription factor and recently the 3D-protein structure of its DNA-binding domain, the T-box, has also been clarified (Kispert et al., 1995; Müller & Herrmann, 1997). Brachyury itself is responsible for the formation and proliferation of undifferentiated precursor cells, of the mesoderm. Other members of the T-box family influence the embryonic development of the neural tube (Tbx6) (Chapman & Papaioannou, 1998) and of the heart (Tbx5) (Li et al., 1997; Spranger et al., 1997). It is probable that still further members of that family are involved in the embryonic patterning of limb development (Simon et al., 1997) and of the brain (T-br1) (Bulfone et al., 1995).

It has been known for some years that that factor (Brachyury) plays a role in early embryonic development and that it is involved in the formation of the so-called "3rd germ layer", the mesoderm. Complete inactivation of the Brachyury factor in mice (Greek: short tail; heterozygous mice have a short tail; another name for the factor is "T", since the gene locus is also called "T-locus") is lethal in early embryonic development and therefore cannot easily be analysed for further influences, for example in the formation of bone and cartilage.

The problem of the invention is now to provide a transcription factor having bone and cartilage cell-forming properties and a human cell for the expression of the factor.

The problem is now solved by a recombinant human cell of undifferentiated mesenchyma for bone and cartilage cell formation, the human cell having the ability to express Tbr-1, Brachyury or another member of the T-box family.

The recombinant human cell can be characterised by Tbx1, Tbx2, Tbx3, Tbx4, Tbx5 or Tbx6 as a member of the T-box family.

Moreover, the recombinant human cell can be characterised in that it was obtained recombinantly from a cell from the following group:

human primary stroma cell of bone marrow,
human primary mesenchymal stem cell,
human primary articular chondrocyte,
human primary chondrocyte from the epiphyses of bones, and
primary human osteoblast.

The recombinant human cell can also be characterised in that the human cell was obtained by biopsy, expanded and altered recombinantly in a manner known per se for the expression of Tbr-1, Brachyury or another member of the T-box family.

In critical tests we have been able to show that in a mesenchymal precursor cell (C3H10T½) recombinantly-expressed Brachyury is able to trigger the formation of bone- and cartilage-forming cells, the osteoblasts and chondrocytes. That test is critical since normal parental C3H10T½ cells are stable tissue cells which, only in response to very different exogenous signals, are capable of forming in four different forms of connective tissue: muscle-forming myoblasts, bone-forming osteoblasts, cartilage-forming chondrocytes and fat-forming adipocytes.

Figure 2:
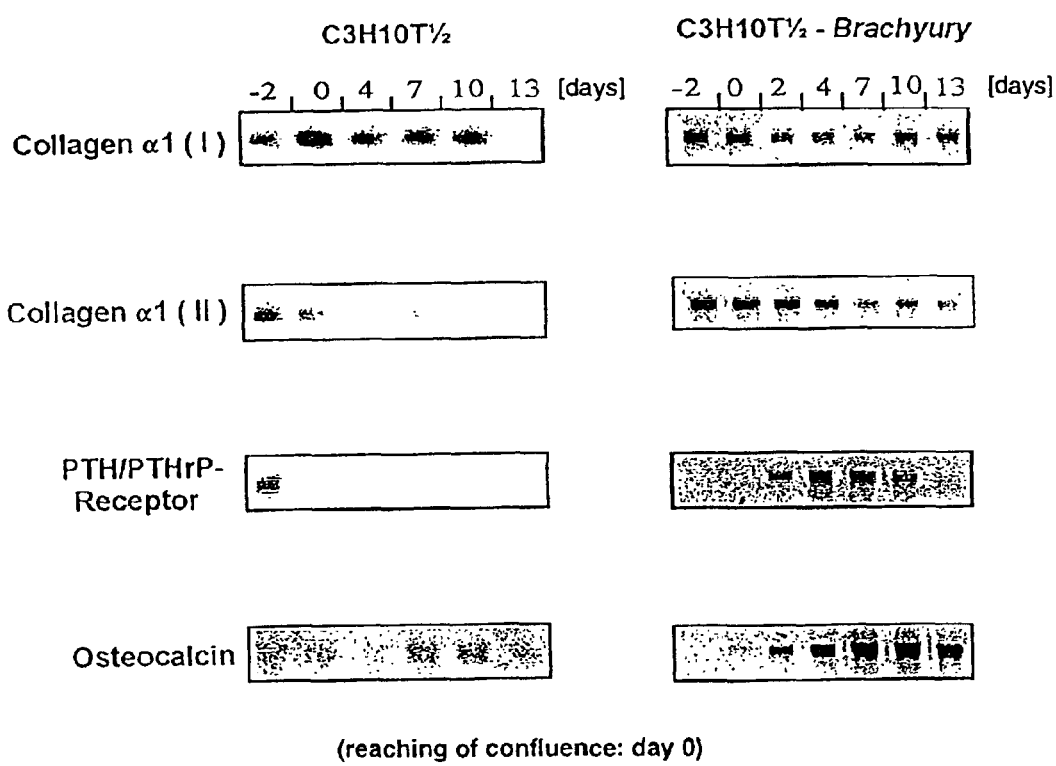

FIGS. 1 and 2 show that Brachyury is now able to trigger the formation of osteoblasts and chondrocytes in those C3H10T½ cells:

FIG. 1

Histologically detectable osteoblasts were detected by means of the enzymatic activity of alkaline phosphatase, a marker gene of those cells. In in vitro culture, the osteoblasts start to mature from day 4 shortly after confluence has been reached (reaching of confluence corresponds to day 0). One week later, distinct chondrocytes stained by Alcian Blue can also be detected.

For the formation of chondrocytes and osteoblasts it is also essential to detect the expression of specific marker genes of both cell forms. In this case the detection was carried out by a procedure called RT-PCR (reverse transcription polymerase chain reaction (PCR)). In that process firstly cDNA is prepared from the total mRNA by reverse transcription, then by means of PCR and specific primers the cDNA for specific marker genes of the osteoblast or chondrocyte formation is amplified and then detected by gel electrophoresis.

FIG. 2

According to the invention it has been shown that highly specific marker genes for osteoblast formation, such as, for example, the osteocalcin gene and the PTH/PTHrP receptor gene, are highly regulated in Brachyury-overexpressing cells. Collagen (I) also exhibits the typically biphase course of osteoblast differentiation. Chondrocyte formation is confirmed by the early high rates of expression of collagen II; moreover it is also probable that the chondrocytes become mature since the formation of collagen (II)-mRNA from day 7 of the culture is down-regulated and other collagens are probably then expressed.

REFERENCES

Bulfone, A., Smiga, S. M., Shimamura, K., Peterson, A., Puelles, L., and Rubenstein, J. L. R. (1995). T-brain-1: A homolog of Brachyury whose expression defines molecularly distinct domains within the cerebral cortex. Neuron 15:63–78.

Chapman, D. L., Garvey N., Hancock, S., Alexiou, M., Agulnik, S. I., Gibson-Brown, J. J., Cebra-Thomas, J., Bollag, R. J., Silver, L. M., and Papaioannou, V. E. (1996). Expression of the T-box family genes, Tbx1–Tbx5, during early mouse development. Dev. Dyn. 206:379–390.

Chapman, D. L. and Papaioannou, V. E. (1998). Three neural tubes in mouse embryos with mutations in the T-box gene Tbx6. Nature 391:695–697.

De Angelis, M. H., Gründker, C. Herrmann, B. G., Kispert, A., and Kirchner, C. (1995). Promotion of gastrulation by maternal growth factor in cultured rabbit blastocysts. Cell Tissue Res. 282:147–154.

Herrmann, B. G., Labeit, S., Poustka, A., King, T. R., and Lehrach, H. (1990). Cloning of the T gene required in mesoderm formation in the mouse. Nature 343:617–622.

Kispert, A., Herrmann, B. G., Leptin, M., and Reuter, R. (1994). Homologs of the mouse Brachyury gene are involved in the specification of posterior terminal structures in Drosophila, Tribolium and Locusta. Genes Dev. 8:2137–2150.

Kispert, A., Koschorz, B., and Herrmann, B. G. (1995). The T protein encoded by Brachyury is a tissue-specific transcription factor. EMBO J. 14:4763–4772.

Li, Q. Y., Newbury-Ecob, R. A., Terrett, J. A., Wilson, D. I., Curtis, A. R. J., Yi, C. H., Gebuhr, T., Bullen, P. J., Robson, S. C., Strachan, T., Bonnet, D., Lyonnet, S., Young, I. D., Raeburn, J. A., Buckler, A. J., Law, D. J., and Brook, J. D. (1997). Holt-Oram syndrome is caused by mutations in TBX5, a member of the Brachyury (T) gene family. Nature Genet. 15:21–29.

Müller, C. W. and Herrmann, B. G. (1997). Crystallographic structure of the T domain DNA complex of the Brachyury transcription factor. Nature 389: 884–888.

Papaioannou, V. E. and Silver, L. M. (1998). The T-box gene family. BioEssays 20: 9–19.

Simon, H. G., Kittappa, R., Khan, P. A., Tsilfidis, C., Liversage, R. A., and Oppenheimer, S. (1997). A novel family of T-box genes in urodele amphibian limb development and regeneration: Candidate genes involved in vertebrate forelimb/hindlimb patterning. Development 124:1355–1366.

Smith, J. (1997). Brachyury and the T-box genes. Curr. Opin. Genet. Dev. 7:474–480.

Spranger, S., Ulmer, H., Troger, J., Jansen, O., Graf, J., Meinck, H. M. and Spranger, M. (1997). Muscular involvement in the Holt-Oram syndrome. J. Med. Genet. 34:978–981.

What is claimed is:

1. An isolated recombinant mammalian mesenchymal stem cell, the mammalian cell expressing exogenous Brachyury wherein expression of said Brachyury leads to formation or proliferation of chondrocytes.

2. The recombinant mammalian cell of claim 1 wherein said cell was obtained by biopsy, before being altered recombinantly to express Brachyury.

* * * * *

UNITED STATES PATENT AND TRADEMARK OFFICE
CERTIFICATE OF CORRECTION

PATENT NO. : 6,908,764 B2
DATED : June 21, 2005
INVENTOR(S) : Stefan Czichos et al.

It is certified that error appears in the above-identified patent and that said Letters Patent is hereby corrected as shown below:

Title page,
Item [73], Assignee, "Yissum Research Development Company, Jerusalem (IL)" should read -- Yissum Research Development Company, Jerusalem (IL) and Gesellschaft fuer Biotechnologische Forschung mbH (GBF), Braunschweig (DE) --.

Signed and Sealed this

Thirteenth Day of September, 2005

JON W. DUDAS
*Director of the United States Patent and Trademark Office*